United States Patent [19]
Kofoed et al.

[11] Patent Number: 5,535,633
[45] Date of Patent: *Jul. 16, 1996

[54] DIFFERENTIAL PRESSURE SENSOR FOR RESPIRATORY MONITORING

[75] Inventors: Scott A. Kofoed; Joseph A. Orr, both of Salt Lake City, Utah

[73] Assignee: Korr Medical Technologies, Inc., Salt Lake City, Utah

[ * ] Notice: The term of this patent shall not extend beyond the expiration date of Pat. No. 5,347,843.

[21] Appl. No.: 287,665

[22] Filed: Aug. 9, 1994

Related U.S. Application Data

[63] Continuation-in-part of Ser. No. 111,161, Aug. 24, 1993, which is a continuation-in-part of Ser. No. 949,573, Sep. 23, 1992, Pat. No. 5,347,843.

[51] Int. Cl.$^6$ .................................................. G01F 1/36
[52] U.S. Cl. ................................ 73/861.052; 73/861.66
[58] Field of Search .......................... 73/861.52, 861.66, 73/861.42

[56] References Cited

U.S. PATENT DOCUMENTS

| | | |
|---|---|---|
| 1,145,220 | 7/1915 | Smith . |
| 2,706,409 | 4/1955 | Preston . |
| 3,410,264 | 11/1968 | Frederik . |
| 3,449,954 | 6/1969 | Brown . |
| 3,581,565 | 6/1971 | Dietrich . |
| 3,590,473 | 7/1971 | Carlson . |
| 3,663,833 | 5/1972 | Pao et al. . |
| 3,726,271 | 4/1973 | Mondshine et al. . |
| 3,752,171 | 8/1973 | Ayre . |
| 3,889,536 | 6/1975 | Sylvester . |
| 3,910,113 | 10/1975 | Brown . |
| 3,937,082 | 2/1976 | Schilling . |
| 3,981,193 | 9/1976 | Goulet . |
| 4,036,054 | 7/1977 | Goulet . |
| 4,047,521 | 9/1977 | Kramer et al. . |

FOREIGN PATENT DOCUMENTS

| | | |
|---|---|---|
| 1509744 | 9/1989 | U.S.S.R. . |
| 699939 | 11/1953 | United Kingdom . |
| 2032118 | 4/1980 | United Kingdom . |
| 2052074 | 1/1981 | United Kingdom . |

OTHER PUBLICATIONS

"Basics of Auto Referencing", Sen Sym, pp. 7–9 through 7–35, undated.
Datex brochure, "See Compliance at a Glance", undated.
*Flow Measurement*, 1991, pp. 124, 125, 474, 475, 477, 500, 558.
Miller, R. W., *Flow Measurement Engineering Handbook*, 1983, pp. 11–5, 11–18, 11–19, 11–26–28.
Miller, R. W., *Flow Measurement Engineering Handbook*, 1989, 16 pages (unnumbered).
Ower, E., et al., "The Characteristics of Pitot and Static Tubes in Incompressible Flow", *The Measurement of Air Flow*, 1966.
Radar, Con, "Pneumotachography", The Perkin Elmer Corporation, California Society of Cardiopulmonary Technologies Conference, Oct. 1982.
Saklad, Meyer, et al., "Pneumotachography: A New, Low–dead space, Humidity–Independent Device", *Anesthesiology*, vol. 5, No. 2, Aug. 1979, pp. 149–153.
Sullivan, William J., et al. "Pneumotachographs: Theory and Clinical Application", *Respiratory Care*, vol. 7, Jul. 1984, pp. 736–749.

*Primary Examiner*—Richard Chilcot
*Assistant Examiner*—Jewel V. Artis
*Attorney, Agent, or Firm*—Trask, Britt & Rossa

[57] ABSTRACT

A differential pressure sensor for measuring respiratory gas flow including a tubular housing having a bore containing a diametrically-oriented, longitudinally extending strut containing first and second lumens having longitudinally spaced pressure ports at axially spaced locations of the strut, the ports being located on opposite sides of a bore restriction.

30 Claims, 3 Drawing Sheets

U.S. PATENT DOCUMENTS

| | | |
|---|---|---|
| 4,154,100 | 5/1979 | Harbaugh et al. . |
| 4,170,134 | 10/1979 | Nathan . |
| 4,345,463 | 8/1982 | Wilson et al. . |
| 4,372,170 | 2/1983 | Dehart et al. . |
| 4,403,514 | 9/1983 | Osborn . |
| 4,481,829 | 11/1984 | Shortridge . |
| 4,546,655 | 10/1985 | Victor . |
| 4,581,945 | 4/1986 | Rusz . |
| 4,823,615 | 4/1989 | Taha . |
| 4,920,808 | 5/1990 | Sommer . |
| 4,957,007 | 9/1990 | Gray . |
| 5,026,255 | 6/1991 | Carpenter et al. . |
| 5,038,773 | 8/1991 | Norlien et al. . |
| 5,088,332 | 2/1992 | Merilainen et al. . |
| 5,137,026 | 8/1992 | Waterson et al. .................... 73/861.52 |
| 5,347,843 | 9/1994 | Orr et al. ............................. 73/861.52 |
| 5,379,650 | 1/1995 | Kofoed et al. ....................... 73/861.52 |

DIFFERENTIAL PRESSURE SENSOR FOR RESPIRATORY MONITORING

This is a continuation-in-part application of prior U.S. application Ser. No. 08/111,161 filed Aug. 24, 1993 which is a continuation-in-part of application Ser. No. 07/949,573 filed Sep. 23, 1992 U.S. Pat. No. 5,347,843.

BACKGROUND OF THE INVENTION

Field of the Invention: The present invention relates to respiratory flow measurement. More specifically, the present invention relates to improved performance of differential pressure flowmeters under diverse inlet conditions through improved sensor configurations.

State of the Art: Respiratory flow measurement during the administration of anesthesia in intensive care environments and in monitoring the physical condition of athletes and other individuals prior to and during the course of training programs provides valuable information for assessment of pulmonary function and breathing circuit integrity. Many different technologies have been applied to create a flowmeter that meets the requirements of the critical care environment. Among the flow measurement approaches which have been employed are:

1) Differential Pressure—measuring the pressure drop or differential across a resistance to flow.
2) Spinning Vane—counting the revolutions of a vane placed in the flow path.
3) Hot Wire Anemometer—measuring the cooling of a heated wire due to airflow passing around the wire.
4) Ultrasonic Doppler—measuring the frequency shift of an ultrasonic beam as it passes through the flowing gas.
5) Vortex Shedding—counting the number of vortices that are shed as the gas flows past a strut placed in the flow stream.
6) Time of Flight—measuring the arrival time of an impulse of sound or heat created upstream to a sensor placed downstream.

Each of the foregoing approaches has various advantages and disadvantages, and an excellent discussion of most of these aforementioned devices may be found in W. J. Sullivan; G. M. Peters; P. L. Enright, M. D.; "Pneumotachographs: Theory and Clinical Application," *Respiratory Care*, July 1984, Vol. 29-7, pp. 736–49, and in C. Rader, *Pneumotachography*, a report for the Perkin-Elmer Corporation presented at the California Society of Cardiopulmonary Technologists Conference, October 1982.

At the present time, the most commonly employed device for respiratory flow measurement is the differential pressure flowmeter. Because the relationship between flow and the pressure drop across a restriction or other resistance to flow is dependent upon the design of the resistance, many different resistance configurations have been proposed. The goal of all of these configurations is to achieve a linear relationship between flow and pressure differential. It should be noted at this point that the terms "resistance" and "restriction" as applied herein to the physical configuration which produces a pressure drop or differential for use as a flowmeter input signal may be used interchangeably.

In some prior art differential pressure flowmeters (commonly termed pneumotachs), the flow restriction has been designed to create a linear relationship between flow and differential pressure. Such designs include the Fleisch pneumotach in which the restriction is comprised of many small tubes or a fine screen, ensuring laminar flow and a linear response to flow. Another physical configuration is a flow restriction having an orifice variable in relation to the flow. This arrangement has the effect of creating a high resistance at low flows and a low resistance at high flows. Among other disadvantages, the Fleisch pneumotach is susceptible to performance impairment from moisture and mucous, and the variable orifice flowmeter is subject to material fatigue and manufacturing variabilities.

U.S. Pat. No. 5,038,773 discloses a differential pressure flowmeter sensor which employs a plurality of pressure ports or apertures symmetrically disposed on the leading and trailing edges of hollow cruciform ribs divided to define two sets of lumens and extending across the cross-section of a tubular housing. U.S. Pat. No. 5,088,332 discloses a differential pressure flowmeter sensor having first and second pressure ports or apertures axially disposed within a tubular housing and supported therein by longitudinally-extending vanes or baffles including surfaces thereon for collecting and guiding pressure generated by gas flowing in the housing to the pressure ports. The flowmeter designs of the foregoing patents are intended to address deficiencies in other prior an flowmeter sensors with regard to performance impairment due to moisture and mucous, and to provide a simple design permitting economical manufacture and, if desired, disposability.

Another type of differential pressure flowmeter sensor is shown in U.S. Pat. No. 4,047,521. Here a sensor comprises a flow tube containing, on diametrically opposite sides, a measuring stud provided with pressure taps and a displacement body facing the stud. The end shapes of both the measuring stud and displacement body may vary.

Yet another type of differential flowmeter sensor is shown in U.S. Pat. No. 4,403,514. In this instance, a flow tube contains a pair of axially spaced pressure ports disposed at right angles to the flow path. A pair of baffles or flow deflectors is disposed in the flow path in alignment with the axes of the pressure ports. Each baffle is positioned at an angle of approximately 45° to the axis of its associated pressure port. The baffles may be either rigidly or resiliently connected to the flow tube depending upon the desired flow characteristic response. In an alternative embodiment, a single circular baffle may be installed between the pressure ports in the flow tube with the center of the baffle being concentric with the axis of the flow tube. In this manner, an annular gap equal to the distance to a pressure port is formed in the flow tube by the circular baffle.

All of the prior art flowmeter sensors referenced above, however, are susceptible to performance impairment and inaccuracies relating to changes in gas flow inlet conditions. In many applications, such variances are avoided or compensated for by employing a flow conditioner, such as a screen or a straight tubing section to provide known flow characteristics to the gas flow entering the sensor. However, in respiratory monitoring applications, the exact geometry of the components "upstream" of the sensor ("tipstream" being bi-directional, as both inspiration and expiration of the patient are monitored) may vary widely based upon the preference of the clinician and the needs of the patient. In addition, the added volume and resistance to flow resulting from the deployment of a flow conditioner diminish respiratory gas exchange, a particularly undesirable situation with anaesthetized patients.

Differential pressure flowmeters of the prior art employing pressure ports which are flush with the conduit wall, spaced therefrom or facing directly into the gas flow are susceptible to localized pressure effects, Bernoulli effects, and pitot tube effects. Pressure port design in the prior art has failed to minimize such effects and to make prior art flowmeters independent of upstream geometry without adding significant volume to the system and/or substantial resistance to flow.

Localized pressure effects arise in flowmeters when gas flow inlet conditions are asymmetrical, such as occurs when a bend is placed in the flow path in close proximity to the sensor, when a jet or nozzle intrudes on the flow stream, or when any non-symmetrical obstruction is placed in the inlet stream.

The Bernoulli effect occurs when fluid flow passes over a tube or other structure placed perpendicular to the direction of flow, the flow over the obstruction causing a vacuum which leads to errors in the measurement of differential pressure across an obstruction to the flow.

The pitot tube effect, or "ram" effect, is related to flow velocity, as the port of a pitot tube faces toward the direction of gas flow. When a nozzle or jet is placed upstream of a sensor, a localized high velocity flow is created in the center of the flow stream, leading to erroneous results in devices of the type disclosed in the prior art.

The flow sensor design of the aforementioned '773 patent is susceptible to error from all of the above phenomena, by virtue of the use of a large number of small pressure ports or apertures placed about the cross-section of the housing bore and the placement of such ports facing the flow direction on the leading edges of the supporting ribs. The '773 sensor is also susceptible to clogging and error from mucous and other patient fluids due to the close proximity of some of the ports to the inner wall of the sensor housing.

The flow sensor design of the aforementioned '332 patent is somewhat less susceptible to clogging from patient fluids due to its axial port location, but is very susceptible to localized pressure effects due to the configuration of the leading faces of the vanes or baffles supporting the pressure ports, which structure collects or focuses the gas flow from across the cross section of the sensor housing bore directly into the pressure ports. This configuration also renders the device of the '332 patent very susceptible to error from the pitot tube effect under certain inlet conditions, and has been demonstrated to unduly limit the dynamic range of the device.

Similarly, the flow sensor design of the '521 patent is susceptible to clogging from patient fluids and varies in response, depending upon the end shape selected for the measuring stud as well as the displacement stud.

The flow sensor design of the '514 patent exhibits very nonlinear pressure output versus flow characteristics. This requires the use of a microprocessor to compensate for the nonlinear pressure/flow characteristics. Also, while compact in design, the sensor requires integral flow straighteners to provide for reliable results when installed in various systems with valving and elbows.

In short, all known prior art differential pressure flow sensors suffer deficiencies when exposed to less than ideal gas flow inlet conditions, and further possess inherent design problems with respect to their ability to sense differential pressure in a meaningful, accurate, repeatable manner over a substantial dynamic flow range, particularly, when it is required for the flow sensor to reliably and accurately measure the respiratory flow rates of infants.

SUMMARY OF THE INVENTION

The present invention comprises a differential pressure sensor for a differential pressure flow meter for respiratory monitoring, the sensor of the invention having the capability of accommodating a wide variety of gas flow inlet conditions while employing a minimum of added system volume or resistance to flow. The design of the sensor of the present invention also substantially prevents the entrance of liquids in the monitoring system into the pressure ports of the sensor.

The sensor of the present invention comprises a substantially tubular housing having disposed in the bore thereof a diametrically-oriented, longitudinally-extending strut having pressure ports located adjacent the axis of the housing and proximate each end of the strut. The pressure ports are each associated with a lumen contained within the strut, the lumens extending to the exterior of the sensor for communication via suitable tubing with a differential pressure transducer. Depending upon whether inspiration or expiration differential pressure is being measured, one port serves as a high pressure tap and the other as a low pressure tap.

In one preferred embodiment, the pressure ports are oriented substantially perpendicular to the axis of the tubular housing, and communicate with the interior volume of the housing via axially-placed notches in the leading and trailing edges of the strut. It is preferred that the notches extend over the entire width of the strut in the area of the pressure ports and through the side faces of the strut so that the pressure ports have reduced response to the velocity of mass flow through the sensor.

In a second preferred embodiment, the pressure ports are oriented substantially perpendicular to the axis of the tubular housing, and are axially spaced along a longitudinal strut located in the bore of the tubular housing. The pressure ports are located on either side of a flow resistance member which is affixed to the strut.

DETAILED DESCRIPTION OF THE PREFERRED EMBODIMENTS

Figure 1:
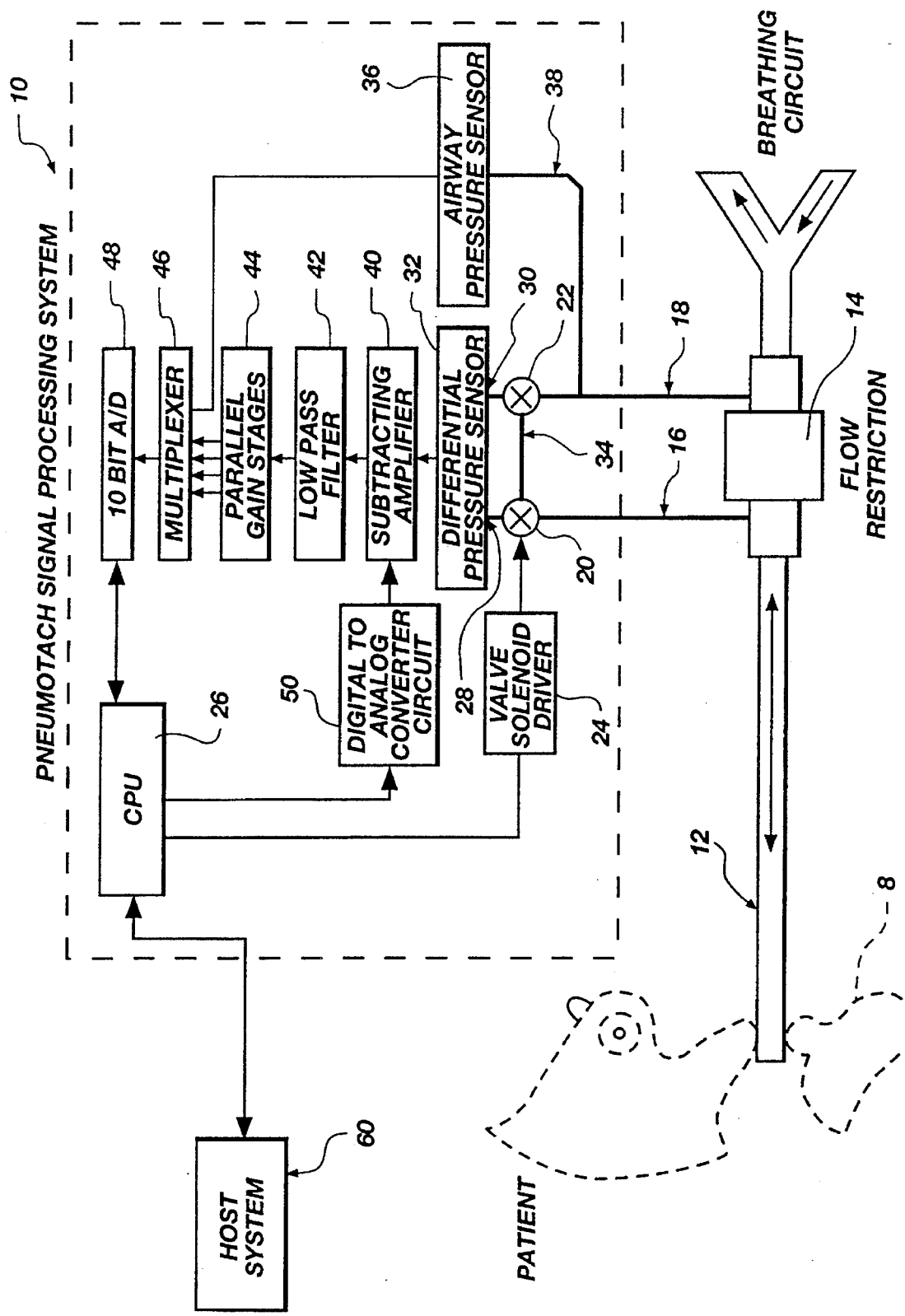
FIG. 1 is a schematic of an apparatus for respiratory flow measurement including a flow sensor according to the present invention, in combination with a differential pressure transducer and signal processing system.

FIG. 1 of the drawings schematically depicts a differential pressure flowmeter 10, with a patient 8 breathing through a respiration tube 12 having a differential pressure sensor 14 according to the present invention employed therewith, the pressures detected by sensor 14 being convened by a differential pressure transducer to an electrical signal, which is then processed as hereinafter described.

First and second pressure takeoff tubes 16 and 18, in respective communication with the interior of sensor 14 on each side of a flow restriction incorporated therein, extend respectively to first and second three-way valves 20 and 22, which are driven by solenoid driver 24 in response to commands from central processing unit (CPU) 26. Valves 20 and 22 are configured to provide communication in a first mode or position from breathing tube 12 through first and second takeoff tubes 16 and 18 to pressure ports 28 and 30 of differential pressure transducer 32 and, in a second mode or position, between ports 28 and 30 through shunt or bypass tube 34 in isolation from respiration tube 12 for auto-referencing.

Airway pressure sensor 36 is in communication with respiration tube 12 through auxiliary pressure takeoff tube 38, which connects to second pressure takeoff tube 18 between valve 22 and respiration tube 12. Differential pressure transducer 32 provides an analog signal to subtracting amplifier 40, which in turn provides a signal to a plurality of amplifiers providing different parallel gain stages 44 through low pass filter 42. The signals from each of the gain stages 44, in conjunction with a signal from airway pressure sensor 36, are received by multiplexer 46 and forwarded to ten bit analog-to-digital converter 48 under control of CPU 26. Digital-to-analog converter circuit 50 is also included in the signal processing system employed in differential pressure flowmeter 10. CPU 26 communicates the signal processing system with a host system 60 such as a personal computer with readout, display and/or alarm means associated therewith.

A preferred embodiment of a gas flow and circuit schematic for flowmeter 10 with parallel gain realization as described above is depicted and described in the previously-referenced U.S. patent applications Ser. No. 949,573 filed Sep. 23, 1992 and Ser. No. 111,161 filed Aug. 24, 1993, both applications being assigned to the assignee of the present invention, and incorporated herein for all purposes by this reference. The '573 application also depicts and describes an alternative embodiment of a gas flow and circuit schematic for flowmeter 10 with series gain realization. However, such circuits and their operation form no part of the differential pressure sensor of the present invention as hereinafter claimed, and therefore no further description thereof will be made in this application.

Figure 2:
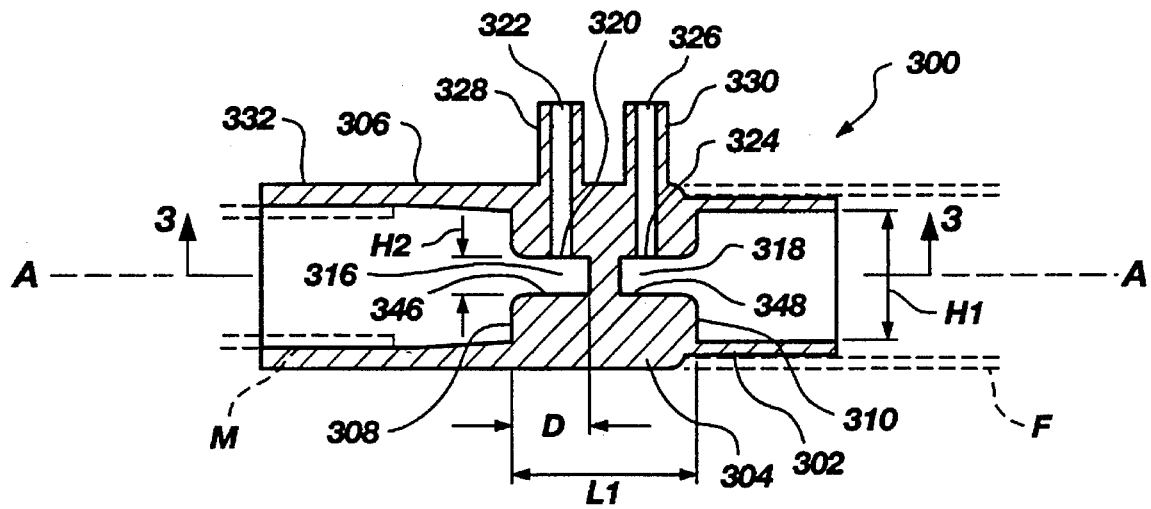
FIG. 2 is a side sectional elevation of a first preferred embodiment of the differential flow sensor of the present invention.
Figure 3:
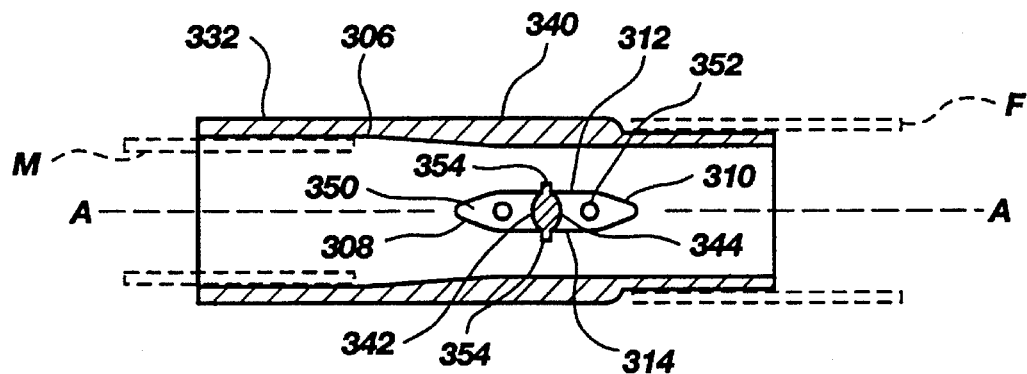
FIG. 3 is a sectional elevation of the sensor configuration of FIG. 2, looking upward from plane 3—3 extending laterally across the axis of the sensor.

Referring now to FIGS. 2 and 3 of the drawings, a preferred embodiment 300 of the differential pressure sensor 14 of the present invention is depicted. Preferred sensor embodiment 300 is preferably a unitary, injection-molded plastic element, so as to afford low manufacturing cost and permit disposal of the sensor after a single use, although this is not a requirement and the materials and method of fabrication are not critical to the invention. Suitable plastics include polycarbonates such as Lexan®, manufactured by General Electric, or Makrolon®, manufactured by Miles Chemicals.

Preferred sensor embodiment 300 includes a tubular housing 302 having a bore of varying diameter, substantially circular cross-section, within which diametrically-oriented, longitudinally-extending strut 304 of axial length L1 and height H1 is disposed. Strut 304, which provides resistance to respiratory gas flow in tubular housing 302, is secured at both ends to the inner wall 306 of housing 302, has first and second end faces 308 and 310 and first and second side faces 312 and 314. The cross-sectional area of strut 304 transverse to the bore axis A should be at least equal to ten percent (10%) of the cross-sectional bore area of the sensor housing 302 at the strut location to provide sufficient restriction to gas flow for effective operation of sensor 300.

It should be noted that the bore diameter of the tubular housing 302 depicted in FIGS, 2 and 3 is different on both ends of strut 304. This is intentional in the preferred embodiment, to accommodate a male connecting tube element shown in broken lines and designated as M on the left-hand side of the sensor, and a female connecting tube element F on the right-hand side of the sensor. Thus, the bore wall 306 tapers from the diameter M to the proximate center of strut 304 to a second, smaller diameter which is substantially constant from the center of the strut 304 to the end of tubular housing 302.

Strut 304 further includes notch means comprising substantially symmetrical notches 316 and 318 located substantially on axis A of housing 302, notches 316 and 318 extending axially inwardly from first and second end faces 308 and 310, respectively, and laterally through first and second sides faces 312 and 314. Pressure port 320 of lumen 322 opens into notch 316, and pressure port 324 of lumen 326 opens into notch 318, lumens 322 and 326 comprising passages internal to strut 304 which extend into and through male luers or nipples 328 and 330 on the exterior surface 332 of tubular housing 302. Flow rate through sensor 300 is proportional to the square root of the differential pressure as measured at ports 320 and 324.

Both pressure ports 320 and 324 face substantially perpendicular to axis A of housing 302, and notches 316 and 318 extend axially inwardly to a depth D at least past pressure ports 320 and 324, and may so extend a distance equal to the height H2 of the notches 316 and 318, which in turn should be less than or equal to four-tenths (4/10) of the height H1 of the strut 304.

As previously noted, resistance to gas flow in embodiment 300 of sensor 14 is created at least by the presence of strut 304 in housing 302, and the width and length of strut 304 may be altered as desired to change flow characteristics. Further resistance to flow is created by reducing the cross-sectional bore area open to flow through housing 302 by necking down the inner wall 306 from diameter M to a smaller diameter as shown at 340 proximate the center of strut 304 and using restrictions 354 as shown on strut 304 in FIG. 3. It is desirable, when necking down the inner diameter of housing 302 as shown at 340, to make a gradual transition in diameter to minimize disruption in the gas flow and also to prevent patient fluids from collecting in the sensor housing 302. It has been found that decreasing the cross-sectional area of housing 302 adjacent inner wall 306 in the vicinity of strut 304 may be effected without impairing the performance characteristics of sensor 14.

It is contemplated that end faces 308 and 310 may be substantially perpendicular to axis A as shown in FIG. 3, chamfered and rounded as shown, so long as the end face configuration is symmetrical when viewed from above. The major characteristic of end faces 308 and 310, aside from symmetry, is that they do not incline toward notches 316 and 318 or otherwise collect or direct flow through sensor 300 toward the notches and pressure ports.

Side faces 312 and 314 of strut 304 am flat as shown in FIG. 3, again the major requirement as with end faces 308 and 310 being one of symmetry between the sides of strut 304.

The back walls 342 and 344 of notches 316 and 318 are arcuate or radiused as shown in FIG. 3, or otherwise symmetrically shaped, as with the end faces 308 and 310.

The floors 346 and 348 and ceilings 350 and 352 are preferably flat as shown in FIG. 2, or may be otherwise symmetrically shaped. Likewise, the transition edges or lines between the end faces 308 and 310 and the notches 316 and 318 are preferably radiused, although alternatively chamfered or bevelled.

The foregoing modifications of the sensor embodiment of FIGS. 2 and 3 may be selectively employed to adapt to the conditions under which the sensor is to operate. In particular, the modification of the cross-sectional flow area in the vicinity of strut 304 may be employed to adjust the dynamic range of sensor 300, as may modifications to the configuration of the end faces, the back walls of the notches, and to the lines of transition between the notches and the end faces and side faces. It is preferred to use laterally extending, transversely oriented center (strut 304) restrictions (ridges or lands) 354 and a gradual inner wall transition in the strut area axial length to add symmetry to the flow pattern, normalize the flow and provide better repeatability of readings. The notch height H2 may be increased to accommodate a wider range of inlet conditions, such as might result from employment of sensor 300 with a variety of endotracheal tubes.

Figure 4:
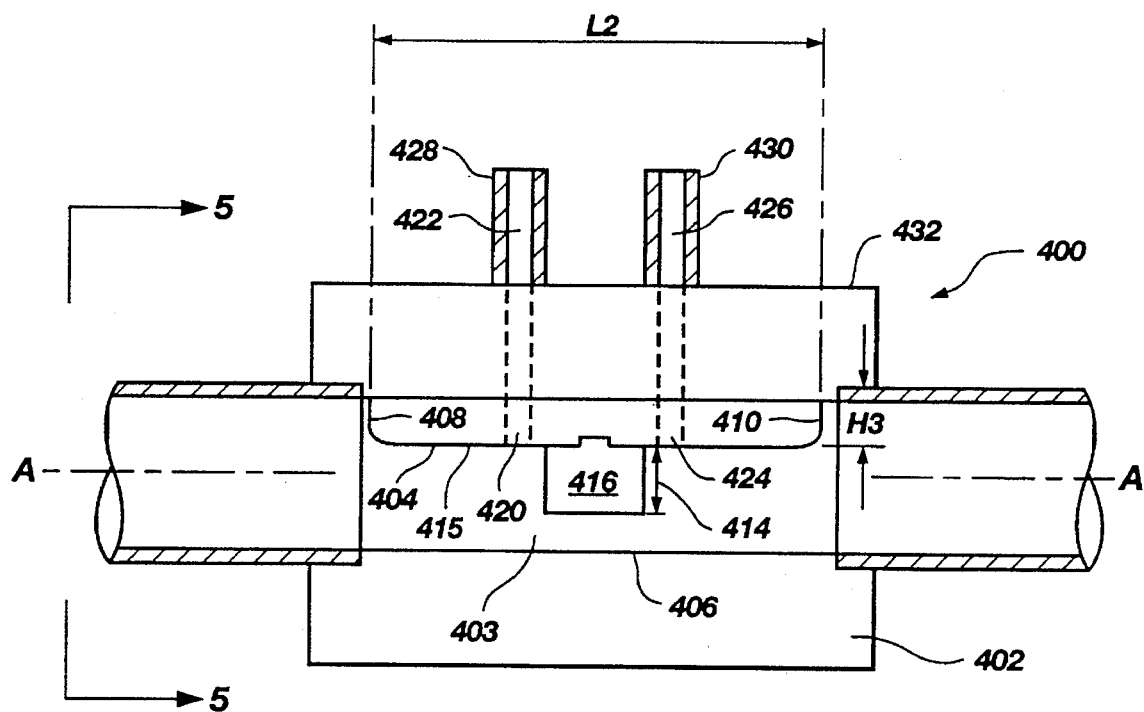
FIG. 4 is a side sectional elevation of a second preferred embodiment of the differential flow sensor of the present invention.

Referring to FIG. 4 of the drawings, a second preferred embodiment 400 of the differential pressure sensor 14 of the present invention is depicted. The preferred sensor embodiment 400 is preferably a unitary injection molded plastic element, so as to afford low manufacturing cost and permit disposal of the sensor after a single use, although this is not a requirement and the materials and method of fabrication are not critical to the invention. As previously stated, suitable plastics include polycarbonates such as Lexan®, manufactured by General Electric, or Makrolon,® manufactured by Miles Chemical.

Preferred sensor embodiment 400 includes a tubular housing 402 having a bore 403 of substantially circular cross-section, within which diametrically-oriented, longitudinally-extending strut 404 of width W1, axial length L2 and height H3 is disposed. Strut 404 is secured to the inner wall 406 of housing 402 at the top thereof, and has first and second end faces 408 and 410, first and second side faces 412 and 414, and longitudinal bore surface 415. The width (WI) and height (H3) dimensions of strut 404 should each be between ten percent (10%) and fifty percent (50%) of the bore diameter of the sensor housing 402 at the strut location to provide sufficient restriction to gas flow for effective operation of sensor 400. The strut should not extend diametrically from the bore wall beyond the center of bore 403, or axis A. It should be noted that strut dimensions and placement, while important to the sensor of the invention, do not significantly contribute to or affect the sensor signal.

Strut 404 carries a flow restriction member comprising a generally cylindrical barrel shaped obstruction member 416 (hereinafter "barrel member") of diameter or height H4 located on strut 404 in the proximate center thereof and extending into the flow area of the tubular housing 402. Pressure port 420 of lumen 422 opens adjacent one end of barrel member 416, while pressure port 424 of lumen 426 open adjacent the other end of barrel member 416, lumens 422 and 426 comprising passages internal to strut 404 which extend into and through male luers or nipples 428 and 430 on the exterior surface 432 of tubular housing 402.

Both pressure ports 420 and 424 face substantially perpendicular to axis A of housing 402, extend axially inward from the ends 408 and 410 of strut 404 a distance at least two diameters of the openings 420 or 424 respectively and are preferably located within an axial distance of barrel member 416 equal to the flow height or diameter H3 thereof within bore 403 of housing 402. The flow area obstruction provided by barrel member 416 should be at least five percent (5%) of the cross-sectional flow area of tubular housing 402.

The resistance to gas flow in embodiment 400 of sensor 14 is created by the presence of strut 404 having barrel member 416 thereon in housing 402, and the height, width and length of the strut as well as the diameter H4 of barrel member 416 may be altered as desired to change flow characteristics. While the barrel member 416 has been described as cylindrical, it may be rectangular in cross-sectional shape or of any other desired cross-sectional geometric shape and sized to yield the desired flow response characteristics. While barrel member 416 has been depicted in FIGS. 4 and 5 as axially disposed in bore 403, it may be placed asymmetrically in the bore, although this is not preferred.

As noted above, it is preferable that the pressure ports 420 and 424 be located within one height or diameter H4 of the ends of barrel member 416. If the pressure ports 420 and 424 are located further than one height or diameter H4 of the barrel member 416 away from the ends of the barrel member 416, the pressure differential response of the embodiment 400 (and attendant signal strength) of sensor 14 decreases.

Also, it is preferable that any valves, elbows, associated flow devices or other obstructions be installed on either side of embodiment 400 of the sensor 14 an axial distance from an end of barrel member 416 equal to at least four diameters of the bore 403 of housing 402.

Figure 5:
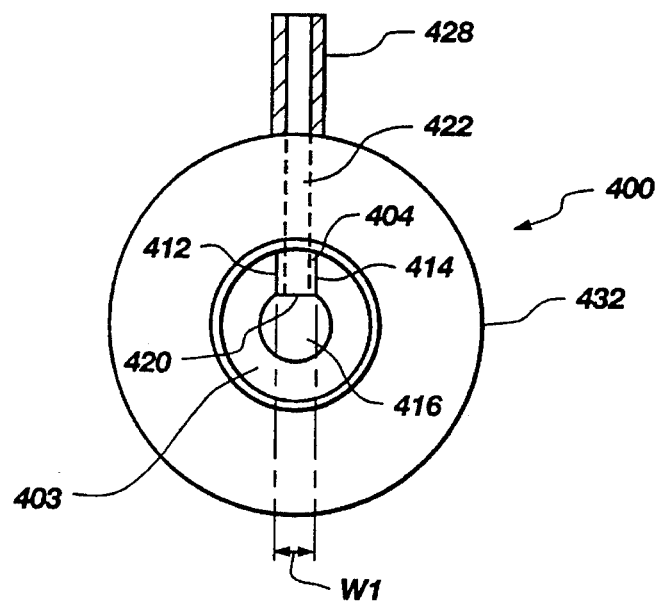
FIG. 5 is an end view of the sensor configuration of FIG. 4.

Referring to FIG. 5 of the drawings, the embodiment 400 is shown in an end view along line 5—5 of FIG, 4 with the lumen 428 shown in cross-sectional view. As shown, the housing 402 is cylindrical in shape as well as barrel member 416 connected to strut 404. The ends 408 and 410 of strut 404 are preferably rounded or curved in shape. However, if desired, although not preferred, they may be rectangular in shape if ports 420 and 424 are sufficiently spaced from ends 408 and 410. The side faces 412 and 414 of strut 404 may be flat or curved.

The differential pressure sensor embodiment is particularly adapted for use in situations where the respiratory flow is extremely small, such as with newborn infants, although it has equal utility in adult respiratory monitoring. The combination of the strut 404 having barrel shaped member 416 located thereon and the location of the pressure ports 420 and 424 provides a particularly effective differential flow measurement sensor for low respiratory rates without being sensitive to fluid accretion. As the embodiment 400 is used with the strut 404 being installed in the top of any flow line, since the bottom of bore 403 of housing 402 is open, any fluid will drain to the bottom of the bore 403 for easy passage and drainage.

While the differential pressure sensor of the present invention has been disclosed herein in terms of a preferred and alternative embodiment and modifications thereto, those of ordinary skill in the art will appreciate that many other additions, deletions and modifications to the disclosed embodiments may be effected without departing from the scope of the invention as hereinafter claimed.

What is claimed is:

1. A differential pressure sensor for measuring respiratory gas flow, said differential pressure sensor comprising:

a tubular housing having a bore and a longitudinal axis;

a strut diametrically disposed and longitudinally extending within said tubular housing bore, said strut having a first end face, a second end face, a first side face, a second side face, an axial length along the longitudinal axis of said tubular housing, and material affixed thereto to restrict said respiratory gas flow through said tubular housing;

first and second longitudinally spaced notch means in said strut located proximate said longitudinal axis of said tubular housing for allowing said respiratory gas flow thereinto, said first notch means extending from said first end face axially inward into said strut and from said first side face to said second side face, said second notch means extending from said second end face axially inward into said strut and from said first side face to said second side face; and first and second pressure ports respectively opening into said first and second notch means from first and second lumens contained within said strut and extending to the exterior of said tubular housing.

2. The differential pressure sensor of claim 1, wherein said first and second pressure ports face substantially perpendicular to said longitudinal axis of said tubular housing.

3. The differential pressure sensor of claim 1, wherein said first and second longitudinally spaced notch means in said strut each include a curved back wall surface portion.

4. The differential pressure sensor of claim 3, wherein said first and second notches extend longitudinally into said strut at least as far as the longitudinally innermost extents of said first and second pressure ports.

5. The differential pressure sensor of claim 1, wherein said notch means have a height perpendicular to said longitudinal axis of said tubular housing less than or equal to about four-tenths of the height of said strut, taken in the same direction.

6. The differential pressure sensor of claim 1, wherein said strut has a cross-sectional area of at least about ten percent of that of the bore of said tubular housing at the location of said strut.

7. The differential pressure sensor of claim 1, wherein said bore of said tubular housing is constricted adjacent the bore wall proximate the location of a portion of said strut.

8. The differential pressure sensor of claim 7, wherein said constriction of said bore comprises a reduction in bore diameter proximate the location of a portion of said strut.

9. The differential pressure sensor of claim 1, wherein said tubular housing bore proximate one longitudinal extent of said strut is greater in diameter than said tubular housing bore proximate the other longitudinal extent of said strut.

10. The differential pressure sensor of claim 1, wherein said strut includes first and second longitudinal ends oriented perpendicular to said longitudinal axis.

11. The differential pressure sensor of claim 1, wherein the first and second longitudinal ends of said strut are rounded.

12. The differential pressure sensor of claim 1, wherein said bore of said tubular housing is constricted between said first and second pressure ports.

13. The differential pressure sensor of claim 12, wherein said constriction is provided by said material and comprises transversely oriented lands extending laterally outwardly from said strut.

14. A differential pressure sensor for measuring respiratory gas flow, said differential pressure sensor comprising:

a tubular housing having a bore and a longitudinal axis;

a strut diametrically disposed in a portion of said tubular housing bore and longitudinally extending within said tubular housing bore, said strut having a first end face, a second end face, a longitudinal bore surface, an axial length along the longitudinal axis of said strut and material affixed to said longitudinal bore surface along a portion of said axial length of said strut to restrict said respiratory gas flow through said tubular housing; and first and second pressure ports respectively opening into said longitudinal bore surface of said strut from first and second lumens contained within said strut and extending to the exterior of said tubular housing, said first and second pressure ports located on first and second sides of said material affixed to said longitudinal bore surface of said tubular housing.

15. The differential pressure sensor of claim 14, wherein said material affixed to said strut is cylindrical in cross-sectional shape.

16. The differential pressure sensor of claim 14, wherein said strut blocks five percent or more of said bore of said tubular housing.

17. The differential pressure sensor of claim 14, wherein said material affixed to said strut blocks five percent or more of said bore of said tubular housing.

18. The differential pressure sensor of claim 14, wherein each end of said strut extends an axial distance beyond each said pressure port of at least two diameters of said pressure port.

19. The differential pressure sensor of claim 14, wherein each said pressure port is located within an axial distance of said material equal to the height above said strut of said material.

20. The differential pressure sensor of claim 14, wherein each end of said strut is aerodynamically shaped.

21. The differential pressure sensor of claim 14, wherein said bore of said tubular housing is substantially constant in diameter.

22. The differential pressure sensor of claim 14, wherein said strut is located in the upper portion of said bore of said tubular housing.

23. The differential pressure sensor of claim 14, wherein the center of said material affixed to said strut is located along said longitudinal axis of said tubular housing.

24. The differential pressure sensor of claim 14, wherein said tubular housing extends a length of at least four bore diameters beyond each axial end of said material located therein.

25. The differential pressure sensor of claim 14, wherein said material is disposed on the axis of said tubular housing bore.

26. The differential pressure sensor of claim 14, wherein said material is of symmetrical shape.

27. The differential pressure sensor of claim 14, wherein said strut extends from a wall of said bore a distance less than or equal to one-half of the diameter of said bore.

28. The differential pressure sensor of claim 14, wherein said strut blocks at least about ten percent or more of said bore of said tubular housing.

29. The differential pressure sensor of claim 14, wherein said strut has a height of between about ten and fifty percent of the diameter of said bore.

30. The differential pressure sensor of claim 14, wherein said strut has a width of between about ten and fifty percent of the diameter of said bore.

* * * * *

UNITED STATES PATENT AND TRADEMARK OFFICE
CERTIFICATE OF CORRECTION

PATENT NO. : 5,535,633

DATED : July 16, 1996

INVENTOR(S) : Kofoed et al.

It is certified that error appears in the above-indentified patent and that said Letters Patent is hereby corrected as shown below:

In column 2, line 13, change "cross- section" to --cross-section--;

In column 2, line 21, after "prior" change "an" to --art--;

In column 5, line 66, change "FIGS," to --FIGS.--;

In column 6, line 54, after "304" change "am fiat" to --are flat--;

In column 6, line 62, after "preferably" change "fiat" to --flat--;

In column 7, line 53, at the beginning of the line change "open" to --opens--;

In column 9, line 62, after "said" change "strut" to --tubular housing,--; and

In column 10, line 10, after "said" change "tubular housing" to --strut--.

Signed and Sealed this

Eleventh Day of February, 1997

Attest:

BRUCE LEHMAN

Attesting Officer

Commissioner of Patents and Trademarks